United States Patent [19]
Dotolo

[11] Patent Number: 5,931,776
[45] Date of Patent: Aug. 3, 1999

[54] SPECULUM HAVING DISSOLVABLE TIP

[75] Inventor: Vincent A. Dotolo, Clearwater, Fla.

[73] Assignee: Dotolo Research Corporation, Pinellas Park, Fla.

[21] Appl. No.: 09/037,275

[22] Filed: Mar. 9, 1998

[51] Int. Cl.⁶ .............................. A61B 1/00; A61M 5/32
[52] U.S. Cl. ........................................... 600/184; 604/265
[58] Field of Search ............................ 600/184; 604/265

[56] References Cited

U.S. PATENT DOCUMENTS

| | | |
|---|---|---|
| 348,843 | 9/1886 | Hamilton ................................ 600/184 |
| 373,361 | 11/1887 | Hamilton ................................ 600/184 |
| 801,924 | 10/1905 | Shiley ...................................... 604/265 |
| 2,027,588 | 1/1936 | Hannon . |
| 2,157,756 | 5/1939 | Irwin . |
| 2,257,072 | 9/1941 | Coombs . |
| 2,420,586 | 5/1947 | De Welles . |
| 2,522,122 | 9/1950 | Kertesz . |
| 3,044,465 | 7/1962 | Anderson et al. . |
| 3,771,522 | 11/1973 | Waysilk et al. . |
| 3,823,714 | 7/1974 | Waysilk et al. . |
| 4,190,059 | 2/1980 | Holt . |
| 4,936,835 | 6/1990 | Haaga ..................................... 604/265 |
| 5,049,138 | 9/1991 | Chevalier et al. ...................... 604/265 |

*Primary Examiner*—Jeffrey A. Smith
*Attorney, Agent, or Firm*—Donald R. Fraser

[57] ABSTRACT

A speculum for use in a colonic lavage which includes a hollow cylindrical body for introducing cleansing fluids into the colon wherein the outermost end of the speculum receives a dissolvable insertable tip to facilitate the initial insertion of the speculum into the anal canal of a patient.

3 Claims, 1 Drawing Sheet

SPECULUM HAVING DISSOLVABLE TIP

BACKGROUND OF THE INVENTION

In the treatment of colitis and ailments caused by the infraction and/or infection of the colon, it has long been known that lavaging of the colon provides beneficial results, and that colonic lavaging mechanisms must be designed to insure comfort and safety for the patient.

Typically, colonic lavage equipment is adapted to be coupled to a building's water plumbing system to obtain hot and cold water pressure. The water is directed to flow through a mixing valve and a temperature gage to enable precision regulations of the water temperature. The water is then directed to flow to a speculum through a pressure regulator valve means provided to limit the maximum pressure of the water and provide for pressure adjustments below the maximum present pressure limit. The water passing through the speculum is provided to continuously irrigate a patient's colon to extract matter lodged therein. The extracted matter will flow with the transient irrigating water back through the speculum into an evacuation line which is coupled to a viewing chamber.

In addition to the apparatus explained above, the system may be provided with a source of oxygen under pressure from an external source which is coupled to the regulator and shutoff valve means upstream of the speculum. In the water and oxygen operating mode, the water is typically aerated in the mixing manifold prior to entry into the speculum. The oxygen line may be replaced by a fluid line which connects an external supply of suitable medicinal fluid which is mixed with the water prior to being directed to the speculum.

SUMMARY OF THE INVENTION

In accordance with the present invention, a new and improved speculum for use with colonic lavage apparatus is disclosed. To insure for the comfort and safety of the patients utilizing colonic lavage apparatus, it is of paramount importance that the speculum is provided with means to enable comfortable and safe insertion of the speculum into the anal canal of the patient.

It is the primary object of the invention to produce a speculum for a colonic lavage apparatus which may be readily and comfortably inserted into the anal canal of a patient.

Another object of the invention is to produce a speculum for a colonic lavage apparatus having an insertable and replaceable tip portion.

Another object of the invention is to produce a tip for a speculum used in colonic lavage which is readily dissolvable

DESCRIPTION OF THE DRAWINGS

The exact manner in which the foregoing objectives and advantages of the invention are achieved in practice will become readily apparent to those skilled in the art when reading the following description of an embodiment of the invention in the light of the accompanying drawings, in which.

DESCRIPTION OF THE ILLUSTRATED EMBODIMENT OF THE INVENTION

Figure 1:
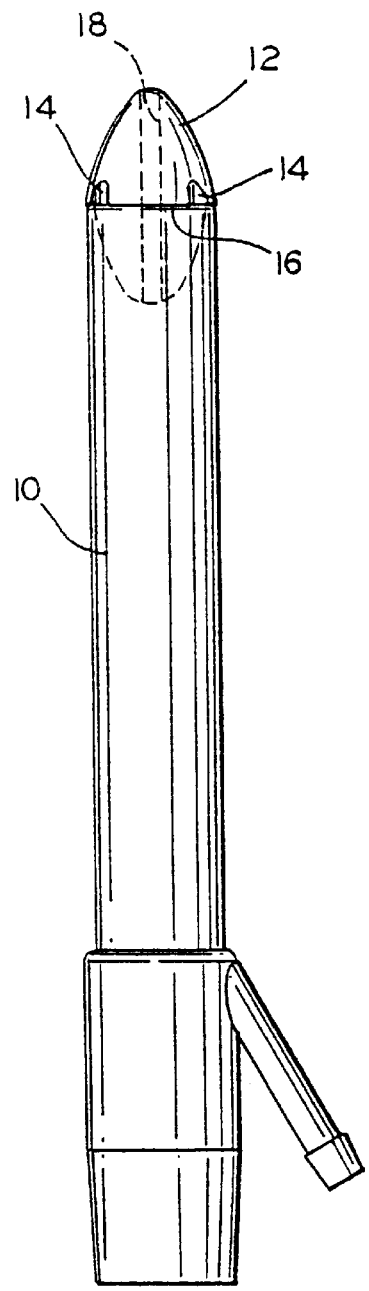
FIG. 1 is an elevational view of a speculum provided with a dissolvable insert tip in accordance with the invention.
Figure 2:
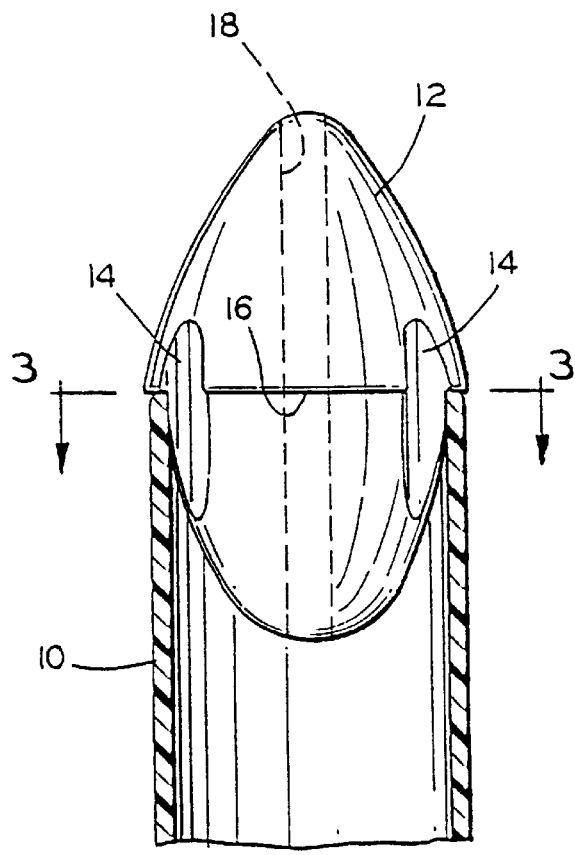
FIG. 2 is an enlarged fragmentary view partially in section illustrating the insert tip illustrated in FIG. 1.
Figure 3:
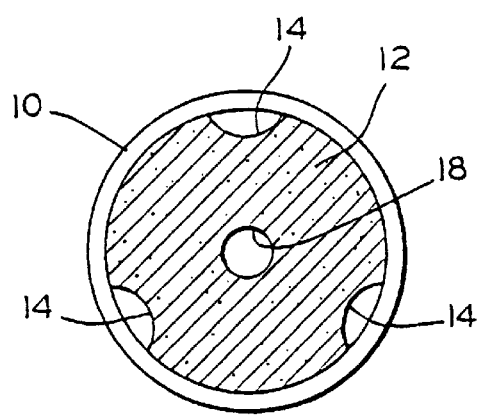
FIG. 3 is a sectional view of the apparatus illustrated in FIGS. 1 and 2 taken along line 3—3 of FIG. 2.

The present invention as illustrated in the drawings relates a speculum 10, the outlet end of which is provided with a dissolvable tip 12. The tip 12 is provided with a plurality of groove-like spaced apart passageways 14 extending generally parallel to the longitudinal axis of the speculum 10.

The tip 12 is further provided with stepped section creating an annular shoulder 16 which extends circumferentially around and radially outwardly beyond the outlet of the speculum at the approximate midpoint of the tip 12. In the assembled form, the shoulder 16 rests against the end of the speculum 10 and will effectively stabilize the tip 12 and prevent any relative rocking movement of the tip 12 with respect to the speculum 10. This feature is particularly important when the speculum 10 is initially being inserted into the anus of the colon. Also, the overlap of the shoulder 16 in respect of the speculum 10 will function to facilitate insertion of the speculum 10.

A centrally formed passageway 18 is provided in the insertable tip 12 to direct fluid flow therethrough from the interior of the speculum 10.

The groove-like passageways 14 are provided to facilitate the outward flow of fluid from the speculum and to expedite the dissolution of the tip 12. Also, the passageways 14 initially provide conduit means for handling the escape of gases and/or fecal matter, when the speculum 10 is initially inserted.

It has been found that the grooves 14 formed in the tip 12 are useful in retaining a lubricant which is typically applied to the tip 12 prior to insertion thereof.

While the speculum 10 can be formed on a variety of different compounds, satisfactory results can be readily achieved by utilizing a compound containing the following ingredients: 1) alfalfa; 2) calcium sulfate; 3) modified cellulose gum; 4) polyplasdone XL; and 5) magnesium stearate. The above compound is safe for injection and rectal insertion in humans. It will be understood that the calcium sulfate, also known as gypsum is used as a non-toxic binder and is water insoluble and not assimilated by the body. The modified cellulose gum is a cellulose derivative used as a stabilizer, texturizer and a non-caloric bulk additive. It is not retained by the body. Polyplasdone SX, also known as crosspovidone XF, is a highly crosslinked polyvinyl pyrrolidone polymer useful as a binder, disintegrant and preservative, not absorbed by the body. The material facilitates the rapid breakup of the compound in water. The magnesium stearate is a water insoluble magnesium soap of stearic acid and assists in the formation of the speculum tip 12 and is not retained by the body.

The speculum tip 12 formed of the above noted substituents tends to dissolve relatively quickly when the transient water flowing through the speculum 10.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A speculum for use in colonic lavage comprising:

a main cylindrical hollow body defining an interior cavity and having at least one outlet; and a dissolvable tip insert for the outlet of said hollow body, said insert being provided with a centrally formed passageway providing communication between said tip and the interior cavity of said body.

2. A speculum as defined in claim 1 wherein said dissolvable tip includes a plurality of longitudinally extending spaced apart axially extending grooves formed therein.

3. A speculum as defined in claim 1 wherein said tip insert is provided with an annular shoulder extending circumferentially around and radially outwardly beyond the outlet of said body.

* * * * *